United States Patent
Liepke et al.

(10) Patent No.: US 7,449,545 B2
(45) Date of Patent: Nov. 11, 2008

(54) ANTIMICROBIAL BOLISIN PEPTIDES

(75) Inventors: Cornelia Liepke, Hannover (DE); Susann Baxmann, Lehrte (DE); Knut Adermann, Hannover (DE)

(73) Assignee: IPF Pharmaceuticals GmbH, Hannover (DE)

( * ) Notice: Subject to any disclaimer, the term of this patent is extended or adjusted under 35 U.S.C. 154(b) by 343 days.

(21) Appl. No.: 10/497,909

(22) PCT Filed: Dec. 4, 2002

(86) PCT No.: PCT/EP02/13724

§ 371 (c)(1),
(2), (4) Date: Jun. 7, 2004

(87) PCT Pub. No.: WO03/048201

PCT Pub. Date: Jun. 12, 2003

(65) Prior Publication Data

US 2006/0252915 A1    Nov. 9, 2006

(30) Foreign Application Priority Data

Dec. 7, 2001  (EP) ................................ 01129094

(51) Int. Cl.
*A61K 38/00*  (2006.01)

(52) U.S. Cl. ............................ 530/326; 514/2; 424/1.69
(58) Field of Classification Search .................... 514/2; 530/326

See application file for complete search history.

(56) References Cited

FOREIGN PATENT DOCUMENTS

| DE | 44 44 753 A | 6/1996 |
| WO | WO 97/35877 | 10/1997 |
| WO | WO 01/94386 A2 | 12/2001 |

OTHER PUBLICATIONS

Terzi, E., Boyot, P., Van Dorsselaer, A., Luu, B., and Trifilieff, E. (1990) Isolation and amino acid sequence of a novel 6.8-kDa mitochondrial proteolipid from beef heart. FEBS Letters 260(1): 122-126.*

* cited by examiner

*Primary Examiner*—Cecilia Tsang
*Assistant Examiner*—Maury Audet
(74) *Attorney, Agent, or Firm*—Jacobson Holman PLLC

(57) ABSTRACT

The invention relates to antibiotically effective peptides which are prepared for medical and commercial use by using biotechnological methods and chemical synthesis. The antibiotically effective peptides can be used in a suitable galenic formulation as medicaments/animal medicaments, food additives or as preservatives for the prevention of microbial contaminations of cosmetics, medical products and requisites.

14 Claims, 1 Drawing Sheet

Figure 1:

Hemolytic activity of bolisine analogues

ANTIMICROBIAL BOLISIN PEPTIDES

This is a nationalization of PCT/EP02/13724 filed Dec. 4, 2002 and published in German.

The invention relates to peptides having a highly effective antimicrobial activity, processes for the preparation thereof, and the use thereof.

It is known that naturally occurring peptides may be antibiotically effective. Thus, WO 97/35877 describes the occurrence and purification of antibiotic peptides from cow's milk, and PCT/EP 01/06518 describes the recovery of antimicrobial peptides from human placenta extract and from bovine thymus extract, and their application.

One of the peptides purified from bovine thymus extract is bolisin (PCT/EP 01/06518, SEQ ID No. 5). Bolisin is a fragment of the bovine mitochondrial proteolipid comprising 17 amino acids, and it inhibits the growth of pathogenic microorganisms in low-salt nutrient media.

It is an object of the invention to provide bolisin-based peptides which have a particularly high specific activity under different conditions. It is also an object of the invention to provide peptides which inhibit the growth of microorganisms in environments with physiological salt concentrations and at the same time have as low as possible a hemolytic activity.

Surprisingly, this object is achieved by providing peptides of the sequence $$R_1 - ZX_3X_3X_1BX_3RX_2X_3X_4BRX_2BX_3X_3B - R_2,$$

wherein $R_1$ represents an amino group ($NH_2$), an amino acid or a peptide having up to 10 amino acids, and $R_2$ represents COOH, $CONH_2$, an amino acid or a peptide having up to 10 amino acids;

Z represents an aromatic amino acid (W, Y, F), preferably tyrosine (Y) or an amino acid mono- or polyhalogenated at the aromatic moiety, preferably tyrosine (Y);

$X_1$ represents arginine (R) or an aromatic amino acid (W, Y, F), preferably tryptophan (W) or an amino acid mono- or polyhalogenated at the aromatic moiety, preferably tryptophan;

$X_2$ represents serine (S), a basic amino acid (R, K), preferably arginine (R), or an aromatic amino acid (W, Y, F), preferably tryptophan (W) or an amino acid mono- or polyhalogenated at the aromatic moiety, preferably tryptophan;

$X_3$ represents threonine (T), a hydrophobic amino acid (I, V, A, L) or arginine (R);

$X_4$ represents aspartic acid (D), proline (P), a basic amino acid (K, R), preferably arginine (R), or an aromatic amino acid (W, Y, F), preferably tryptophan (W) or an amino acid mono- or polyhalogenated at the aromatic moiety, preferably tryptophan; and B represents a basic amino acid (K, R).

The invention also relates to derivatives and/or fragments of the peptides according to the invention having antimicrobial activity, especially the derivatives and/or fragments which are amidated, acylated, acetylated, alkylated, sulfated, phosphorylated, halogenated, especially halogenated at aromatic amino acid side chains, glycosylated, oxidized, modified by esterification or lactone formation, and/or cyclized. Halogenated peptides are preferably halogenated at aromatic residues of amino acid side chains. The amino acids are designated with the one-letter code.

Preferably, the peptides according to the invention have the following sequences:

$R_1-ZIX_3X_1BX_3RX_2ADBRX_2BALB-R_2$
(Sequence ID Nos.: 2, 4, 8, 12, 13, 15)

$R_1-ZIX_3X_1BX_3RX_2APBRX_2BALB-R_2$
(Sequence ID No.: 11)

$R_1-ZIX_3X_1BX_3RX_2ABBRX_2BALB-R_2$
(Sequence ID Nos.: 1, 3, 5, 6, 7, 9, 10, 18, 21-24, 28, 29, 31, 32, 35, 38, 41, 45, 47, 48, 51)

$R_1-ZIX_3X_1BX_3RX_2AZBRX_2BALB-R_2$
(Sequence ID Nos.: 14, 16, 17, 19, 20, 25-27, 30, 33, 34, 36, 37, 42-44, 46, 49, 50, 52, 53, 54)

$R_1-ZIX_3X_1BX_3RX_2TZBRX_2BALB-R_2$
(Sequence ID No.: 55)

wherein $X_3$ represents a hydrophobic amino acid (I, V) or arginine (R), and $R_1$, $R_2$, Z, $X_1$, $X_2$ and B have the meanings as stated above. Preferred peptides of the invention are listed in Table 1. The invention also relates to their derivatives and/or fragments having antimicrobial activity, especially the derivatives and/or fragments which are amidated, acylated, acetylated, alkylated, sulfated, phosphorylated, halogenated, glycosylated, oxidized, modified by esterification or lactone formation, and/or cyclized.

The invention comprises the peptides modified by esterification or lactone formation as well as the peptides according to the invention which have been reacted at a free amino group with activated polyoxyalkylene glycol or a conjugate of a polyoxyalkylene glycol and, for example, a fatty acid. Preferred are fatty acids having a chain length of from 12 to 18 carbon atoms and polyoxyethylene as the polyoxyalkylene glycol having a chain length of from 2 to 100. More preferred are activated polysorbate esters and their derivatives. The peptide conjugates are prepared for improving the pharmacological properties of the peptides.

In addition to the derivatives mentioned, the peptides may also comprise the corresponding D-amino acids instead of the natural L-amino acids, as well as iminoamino acids and rare amino acids, such as hydroxylysine, homoserine and ornithine. Further, the invention comprises the retro, inverso and retro-inverso peptides. "Retro peptides" means the peptides according to the invention having a reverse amino acid sequence, "inverso peptides" means the peptides according to the invention which consist of D-amino acids, and "retro-inverso peptides" means those peptides which have a reverse amino acid sequence formed from D-amino acids.

The invention also relates to peptide mimetics of the peptides according to the invention. These are characterized by a modification of one or more peptide bonds, for example, by a reverse peptide bond or by an ester bond.

The bolisin analogues according to the invention are cationic peptides having antibiotic activity. The bolisin analogues contain at least 9 and at most 37 amino acid residues, preferably not more than 20 amino acid residues.

The peptide analogues of bolisin according to the invention have a clearly increased antimicrobial activity. The peptides described in the present invention also effectively inhibit the growth of pathogenic germs in nutrient media which have a physiological salt concentration and therefore, in contrast to the naturally occurring bolisin, can be used for a wide variety of applications. Human pathogenic germs with antibiotic resistance are also killed at low peptide concentrations.

As the fragments, there may be used, in particular, N-terminally or C-terminally truncated peptides, but also peptides in which individual amino acids are deleted, preferably not more than 10% of the amino acids. The invention relates to these fragments to the extent where they have antimicrobial properties. "Antimicrobial properties" of the fragment means that the fragment has at least 50% of the activity of the parent peptide, i.e., at most requires double the inhibitory concentration. The test microorganisms employed are either *Staphylococcus aureus* or *Escherichia coli*, depending on against which microorganism the peptide exhibits a better activity. The microorganisms are characterized as follows:
*Staphylococcus aureus*: Gram-positive cocci, ATCC 25923;
*Escherichia coli*: Gram-negative rods, ATCC 25922.

The invention also comprises nucleic acids which code for the peptides according to the invention, and vectors and plasmids which contain such nucleic acids.

The invention also relates to a medicament which contains one or more peptides according to the invention.

The peptides according to the invention are suitable for the treatment of diseases caused by misplaced microbial colonizations, such as infections, inflammations, microbially induced tumors, microbially caused degenerative diseases, diarrheic diseases, colics, deviations in the oral, intestinal and vaginal floras, caries, sepsis, toxic shock conditions. The misplaced microbial colonization may be caused, for example, by bacteria, fungi, yeasts, protists, viruses, mycoplasmas, filariae and/or plasmodiums. They may be employed in both acute and chronic diseases of humans and animals.

The peptides according to the invention are preferably used in medicinal formulations. The medicinal formulation contains one or more of the peptides according to the invention, or a physiologically acceptable salt of the peptides. Medicinal formulations can contain pharmaceutically usual auxiliary agents which contribute, for example, to the solubility, stability or sterility of the medicament or increase the efficiency of uptake into the body. Further, other antibiotic substances may be contained, for example, from the group of penicillins, cephalosporins, carbacephems, cephamycins, carbapenems, quinolones, tetracyclines, aminoglycosides, macrolides, glycopeptides, chloroamphenicols, glycylcyclines, licosamides, fluoroquinolones and peptide antibiotics.

The form and composition of the medicament which contains the peptides depends on the route of administration. Preferably, galenic formulations and application forms are selected in which the peptides arrive at the target site in a non-degraded condition. The peptides can be administered enterally, parenterally, intranasally, orally and by inhalation. Preferably, the peptides are packaged with an injection preparation either as a solution or as a lyophilizate for dissolution immediately before use. The peptides can be, for example, injected intravenously, injected or implanted intraperitoneally, injected or implanted subcutaneously, injected intradermally, injected or implanted intramuscularly, injected intrathecally, inhaled (aerosol, spray) or applied topically (e.g., creams, ointments, eyedrops, eardrops, shampoos). Bolisin analogues can be administered locally as injection, drops, spray, tablets, suppositories, cream, ointments, gel etc. It is possible to perform the administration as a bolus or repeatedly over a period of time.

The dose of the peptides to be administered depends on the indication and the application of particular derivatives. Preferably, the peptides according to the invention are employed in amounts of from 0.1 to 100 mg/kg of body weight.

The invention also relates to a diagnostic agent which contains peptides or nucleic acids according to the invention.

The peptides according to the invention may also be used as additives to foodstuffs. They may be used in the preparation of foodstuffs as auxiliary agents, especially for foodstuffs which are prepared by fermentation and other bacterial processes. The preparations according to the patent are natural preservatives. Further possibilities of the application of the peptides according to the invention are the use as disinfectants for all situations in which microorganisms are not desired. Examples thereof are the application for the surface disinfection or as a coating of medicinal products, air filters and requisites, such as clothing and jewels. "Medicinal products" means all medical auxiliaries which are applied to the patient, such as implants, prostheses, stents, tubes, cannulas, catheters, synthetic vascular systems, artificial heart valves and needles. The term "medicinal products" further includes containers for the storage of blood or blood components as well as containers for organ shipping etc. Further, it is possible to use the peptides in water processing, or as a component of shampoos and soaps, as food additives, cosmetic preservatives, additives for the preservation of cell culture media etc. and as a plant protection agent.

EXAMPLES

Chemical Synthesis of Bolisin Analogues

The peptide synthesis of bolisin analogues is based on the standard method of solid-phase Fmoc strategy. For the automated synthesis, an ABI 433 A Synthesizer (Applied Biosystems, Weiterstadt, Germany) was used. An Fmoc-Lys(boc) Wang resin served as the solid phase. During the peptide synthesis, the individual coupling steps were checked to ensure that each amino acid was incorporated in a high yield. Peptides were cleaved from the resin with 94% trifluoroacetic acid (TFA), 3% ethanedithiol and 3% water and subsequently purified by chromatography.

For the chromatographic purification, reverse phase (RP) HPLC was applied. A preparative RP C18 column (PrepPAK 500 C18, 47×300 mm) served as the solid phase, and acetonitrile served as eluant (mobile solvent A: 0.07% TFA in water; mobile solvent B: 80% acetonitrile/0.07% TFA in water). At a flow rate of 40 ml/min, the peptides were eluted from the solid phase by the gradient method (increment of 0.5% mobile solvent B per min in the eluant) and detected at a wavelength of 215 nm.

The synthetic peptides were analyzed by mass spectrometry. The purity of the peptides was checked by capillary zone gel electrophoresis and analytical reverse-phase HPLC (purity≧95%). The amino acid sequence of the peptides was verified by automated Edman degradation.

The amino acid sequences of the synthesized bolisin analogues according to the invention are stated in Table 1 using the one-letter code.

TABLE 1

| Name | SEQ ID No. | Sequence |
|---|---|---|
| BOL-6 | 2 | YIVYKIRSARKRSKALK |
| BOL-7 | 2 | YIVYKIRSADKRRKALK |
| BOL-11 | 3 | YIVYKRRSARKRSKALK |
| BOL-12 | 4 | YIVYKRRSADKRRKALK |
| BOL-13 | 5 | YIVYKIRSARKRRKALK |
| BOL-14 | 6 | YIRYKIRSARKRRKALK |

TABLE 1-continued

| Name | SEQ ID No. | Sequence |
|---|---|---|
| BOL-15 | 7 | YIVYKRRSARKRRKALK |
| BOL-16 | 8 | YIRYKRRSADKRRKALK |
| BOL-17 | 9 | YIRYKIRSARKRRKALK |
| BOL-18 | 10 | YIRYKRRSARKRRKALK |
| BOL-21 | 11 | YIVYKIRSAPKRSKALK |
| BOL-25 | 12 | YIVWKIRSADKRSKALK |
| BOL-27 | 13 | YIVYKIRWADKRSKALK |
| BOL-29 | 14 | YIVYKIRSAWKRSKALK |
| BOL-30 | 15 | YIVYKIRSADKRWKALK |
| BOL-44 | 16 | YIVYKIRSAWKRRKALK |
| BOL-45 | 17 | YIVYKIRSAWKRWKALK |
| BOL-46 | 18 | YIVYKIRSARKRWKALK |
| BOL-47 | 19 | YIVYKIRWAWKRSKALK |
| BOL-48 | 20 | YIVYKIRWAWKRRKALK |
| BOL-49 | 21 | YIVYKIRWARKRSKALK |
| BOL-50 | 22 | YIVYKIRWARKRRKALK |
| BOL-51 | 23 | YIVYKIRWARKRWKALK |
| BOL-52 | 24 | YIVYKIRRARKRRKALK |
| BOL-53 | 25 | YIVYKIRRAWKRSKALK |
| BOL-54 | 26 | YIVYKIRRAWKRRKALK |
| BOL-55 | 27 | YIVYKIRRAWKRWKALK |
| BOL-56 | 28 | YIVYKIRSAKKRKKALK |
| BOL-57 | 29 | YIVYKIRSAKKRWKALK |
| BOL-58 | 30 | YIVYKIRSAWKRKKALK |
| BOL-59 | 31 | YIVYKIRWAKKRKKALK |
| BOL-60 | 32 | YIVYKIRWAKKRWKALK |
| BOL-61 | 33 | YIVYKIRWAWKRKKALK |
| BOL-67 | 34 | YIVYKIRSAWKRWKAL |
| BOL-68 | 35 | YIVYKIRSARKRWKAL |
| BOL-69 | 36 | YIVYKIRSAWKRRK |
| BOL-70 | 37 | YIVYKIRSAWKRWK |
| BOL-71 | 38 | YIVYKIRSARKRWK |
| BOL-72 | 39 | YIVYKIRWARKRRKAL |
| BOL-73 | 40 | YIVYKIRWARKRRK |
| BOL-74 | 41 | YIVWKIRSARKRRKALK |
| BOL-75 | 42 | YIVWKIRSAWKRSKALK |
| BOL-79 | 43 | YIVRKIRSAWKRWKALK |
| BOL-80 | 44 | YIVRKIRSAWKRRKALK |

TABLE 1-continued

| Name | SEQ ID No. | Sequence |
|---|---|---|
| BOL-81 | 45 | YIVWKIRSARKRWKALK |
| BOL-82 | 46 | YIVWKIRSAWKRWKALK |
| BOL-83 | 47 | YIVRKIRSARKRRKALK |
| BOL-84 | 48 | KYIVYKIRSARKRRKALK |
| BOL-85 | 49 | KYIVYKIRSAWKRSKALK |
| BOL-86 | 50 | KYIVYKIRSAWKRRKALK |
| BOL-87 | 51 | KYIVYKIRWARKRRKALK |
| BOL-91 | 52 | YIVYKIRFAFKRSKAL |
| BOL-92 | 53 | YIVYKIRFAFKRRKAL |
| BOL-93 | 54 | YIVYKIRWAWKRSKAL |
| BOL-97 | 55 | YIVYKIRWTWKRSKAL |
| BOL-103 | 56 | KLAKRRKWAWRIKYVIY |

Examination of the Antimicrobial Effectiveness of Bolisin Analogues

The bolisin analogues of the present invention were examined for their suitability as antibiotic therapeutical agents by means of various biological tests. Thus, the chemically synthesized peptides were examined for their antimicrobial effectiveness against three Gram-positive and three Gram-negative bacterial strains as well as against a yeast.

The following microorganisms were used:

Gram-positive: *Staphylococcus aureus* ATCC 25923
  *Enterococcus faecalis* ATCC 51299 (vancomycin-resistant)
  *Streptococcus pneumoniae* DSM 11865 (penicillin-resistant)

Gram-negative: *Escherichia coli* ATCC 25922
  *Pseudomonas aeruginosa* ATCC 9027
  *Klebsiella pneumoniae* ATCC 10031

Yeast: *Candida albicans* ATCC 10231

The antibiotic activity of bolisin analogues was examined by determining the minimum inhibition concentration. The minimum inhibition concentration of an analogue designates the lowest peptide concentration which is required to inhibit the growth of microorganisms completely after an incubation time of 18±2 h. This method allows to obtain a quantitative result about the antimicrobial potency of the peptides. These examinations were performed by analogy with the recommendations (M7-A3) edited by the NCCLS (National Committee for Clinical Laboratory Standards) by applying a dilution test in a liquid medium using chemically synthesized peptides (peptide sequences according to claims 1 to 3). Mueller Hinton Broth was used as the test medium according to the NCCLS recommendations unless indicated otherwise. Table 2 shows the antimicrobial activity of the peptide analogues, which is clearly improved as compared to the parent peptide bolisin. The minimum inhibition concentrations are stated in [μg/ml].

TABLE 2

| Microorganisms | 1 | 2 | 3 | 4 | 5 | 6 | 7 |
|---|---|---|---|---|---|---|---|
| Bolisin* | >300 | >300 | >300 | >300 | >300 | >300 | nd |
| Bolisin | >300 | >300 | >300 | >300 | >300 | >300 | >300 |
| Bolisin** | 25 | 300 | 300 | 6.25 | 150 | 150 | nd |
| BOL-6* | 37.5 | 200 | 150 | 37.5 | (9.375) | 37.5 | nd |
| BOL-7* | 75 | >300 | >300 | 150 | (75) | 300 | nd |
| BOL-11* | 37.5 | >300 | >300 | 37.5 | (150) | 150 | nd |
| BOL-12* | 18.75 | >300 | >300 | 18.75 | (300) | 200 | nd |
| BOL-13* | 18.75 | 75 | 150 | 18.75 | (9.375) | 18.75 | nd |
| BOL-14* | 50 | >300 | >300 | 37.5 | (150) | 75 | nd |
| BOL-15* | 18.75 | >300 | >300 | 18.75 | (150) | 75 | nd |
| BOL-16* | 100 | >300 | >300 | 75 | (300) | 150 | nd |
| BOL-17* | 37.5 | 200 | 300 | 37.5 | 200 | 9.375 | nd |
| BOL-18* | 18.75 | >300 | >300 | 18.75 | 300 | 37.5 | nd |
| BOL-21* | 75 | >300 | >300 | 150 | (150) | 200 | nd |
| BOL-25* | 150 | >300 | >300 | 150 | (150) | 200 | nd |
| BOL-27* | 75 | 300 | 300 | 75 | (150) | 150 | nd |
| BOL-29* | 9.375 | 75 | 150 | 9.375 | (18.75) | 50 | nd |
| BOL-30* | 100 | >300 | >300 | 150 | (300) | 300 | nd |
| BOL-44 | 150 | >300 | 200 | 200 | (75) | 75 | 37.5 |
| BOL-45 | 18.75 | 100 | 100 | 12.5 | (25) | 4.7 | 18.75 |
| BOL-46 | 300 | 200 | 200 | 200 | (100) | 150 | 150 |
| BOL-47 | 18.75 | 25 | 18.75 | 18.75 | (25) | 9.375 | 18.75 |
| BOL-48 | 9.375 | 12.5 | 9.375 | 18.75 | 200 (6.5) | 4.7 | 9.375 |
| BOL-49 | 75 | 25 | 18.75 | 50 | (12.5) | 18.75 | 18.75 |
| BOL-50 | 37.5 | 25 | 18.75 | 50 | (6.25) | 9.375 | 9.375 |
| BOL-51 | 37.5 | 25 | 12.5 | 50 | 300 (25) | 18.75 | (18.75) |
| BOL-52 | 300 | 200 | 200 | >300 | (37.5) | 75 | (37.5) |
| BOL-53 | 150 | 200 | 200 | 200 | (75) | 100 | (37.5) |
| BOL-54 | 200 | 100 | 75 | 100 | (25) | 18.75 | 18.75 |
| BOL-55 | 12.5 | 50 | 37.5 | 12.5 | (9.375) | 3.125 | 9.375 |
| BOL-56 | >300 | >300 | >300 | >300 | (200) | 300 | (300) |
| BOL-57 | >300 | >300 | >300 | >300 | (200) | 300 | 300 |
| BOL-58 | >300 | >300 | 300 | >300 | (100) | 100 | (75) |
| BOL-59 | 50 | 50 | 50 | 150 | (18.75) | 18.75 | (9.375) |
| BOL-60 | 50 | 25 | 50 | 100 | (18.75) | 18.75 | (18.75) |
| BOL-61 | 37.5 | 25 | 25 | 25 | 300 (75) | 18.75 | 9.375 |
| BOL-67 | 25 | 100 | 100 | 25 | (50) | 37.5 | 18.75 |
| BOL-68 | 200 | 200 | 300 | 200 | (200) | 300 | 200 |
| BOL-69 | 300 | 150 | 200 | 150 | (200) | 300 | 37.5 |
| BOL-70 | 100 | 150 | 150 | 100 | (100) | 75 | 37.5 |
| BOL-71 | 200 | 200 | 300 | 300 | (200) | 300 | 300 |
| BOL-72 | 75 | 25 | 18.75 | 100 | (12.5) | 18.75 | 18.75 |
| BOL-73 | 37.5 | 25 | 18.75 | 50 | (9.375) | 18.75 | 9.375 |
| BOL-74 | 300 | 150 | 150 | 300 | (12.5) | 18.75 | 75 |
| BOL-75 | 150 | 200 | 150 | 75 | (37.5) | 75 | 37.5 |
| BOL-79 | 9.375 | >300 | 300 | 3.125 | (4.7) | 2.35 | 4.7 |
| BOL-80 | >300 | >300 | >300 | >300 | (18.75) | 150 | 37.5 |
| BOL-81 | 300 | 150 | 75 | 300 | (18.75) | 25 | 75 |
| BOL-82 | 18.75 | 75 | 37.5 | 18.75 | (9.375) | 12.5 | 9.375 |
| BOL-83 | >300 | >300 | >300 | >300 | >300 | >300 | 300 |
| BOL-84 | >300 | >300 | 300 | >300 | (75) | 75 | 37.5 |
| BOL-85 | >300 | 300 | 300 | >300 | (37.5) | 150 | 75 |
| BOL-86 | 75 | 200 | 150 | 150 | (18.75) | 50 | 18.75 |
| BOL-87 | 9.375 | 37.5 | 9.375 | 18.75 | (9.375) | 9.375 | 9.375 |
| BOL-91 | 25 | 37.5 | 37.5 | 25 | (150) | 18.75 | nd |
| BOL-92 | 18.75 | 18.75 | 25 | 18.75 | (37.5) | 12.5 | nd |
| BOL-93 | 25 | 37.5 | 25 | 25 | (37.5) | 25 | nd |
| BOL-97 | 12.5 | 18.75 | 18.75 | 18.75 | (37.5) | 18.75 | nd |
| BOL-103 | 18.75 | 37.5 | 37.5 | 18.75 | (9.4) | 18.75 | nd |

*Test medium: half-concentrated Mueller Hinton Broth
**Test medium: 3 g/l Tryptic Soy Broth (low ion strength medium)

Values in parentheses designate a 75% inhibition of the growth of the microorganisms at the peptide concentration stated. A complete growth inhibition could not be achieved in this case. For determining the minimum inhibition concentration, the following microorganisms were used:

1. *Staphylococcus aureus* ATCC 25923
2. *Enterococcus faecalis* ATCC 51299 (vancomycin-resistant)
3. *Streptococcus pneumoniae* DSM 11865 (penicillin-resistant)
4. *Escherichia coli* ATCC 25922
5. *Pseudomonas aeruginosa* ATCC 9027
6. *Klebsiella pneumoniae* ATCC 10031
7. *Candida albicans* ATCC 10231

The peptides according to the invention effectively inhibit the growth of both Gram-positive and Gram-negative bacteria as well as of yeasts. Human pathogens, such as *Staphylococcus aureus, Escherichia coli, Pseudomonas aeruginosa* and *Klebsiella pneumoniae*, were effectively killed. Of particular importance is the very effective growth inhibition of bacteria having an existing antibiotic-resistance, such as *Streptococcus pneumoniae* (penicillin-resistant) and *Enterococcus faecalis* (vancomycin-resistant). The potency of action of the bolisin analogues is manifoldly better than that of the parent peptide bolisin.

Examination of the Effectiveness at Increased Salt Concentration

Also for these examinations, the minimum inhibition concentration of the peptides against Gram-positive and Gram-negative microorganisms (microorganisms 1-6) was determined. Tryptic Soy Broth (3 g/l) with an addition of salt in physiological concentration (150 mM sodium chloride) was used as the test medium. Table 3 shows the antimicrobial activity of the peptide analogues in a salt-containing medium, which is also significantly improved over that of the parent peptide bolisin.

whereas the cells of the host should remain unaffected. As a simple model for the examination of the cytotoxic effect of a peptide on eukaryotic cells, the hemolysis test is used in which the lysing and thus toxic activity of the peptides against red blood cells (erythrocytes) is examined. The procedure for determining the hemolytic activity of the peptides was performed by analogy with Helmerhorst et al. (Helmerhorst et al., 1999, FEBS Lett. 449: 105-110).

Erythrocytes were isolated from the citrate-containing whole blood of a healthy subject by centrifugation (1500×g, 20° C., 10 min) and diluted 200 fold with test medium. Peptides were added at various concentrations to a 96 well microtitration plate with V-shaped bottoms and incubated with the diluted erythrocyte suspension at 37° C. for 1 h. The erythrocytes were separated by a subsequent centrifugation (1000×g for 5 min). The supernatants colored from released

TABLE 3

| Microorganisms | 1 | 2 | 3 | 4 | 6 |
|---|---|---|---|---|---|
| Bolisin | >300 | >300 | >300 | >300 | >300 |
| BOL-44 | 200 | (300) | >300 | 150 | >300 |
| BOL-45 | 37.5 | 200 | 200 | 75 | 4.7 |
| BOL-46 | >300 | >300 | >300 | >300 | >300 |
| BOL-47 | 18.75 | 50 | 37.5 | 25 | 9.375 |
| BOL-48 | 18.75 | 18.75 | 25 | 9.375 | 9.375 b |
| BOL-49 | 75 | 75 | 100 | 50 | 75 |
| BOL-50 | 37.5 | 50 | 50 | 37.5 | 37.5 |
| BOL-51 | 75 | 37.5 | 37.5 | 37.5 | 25 |
| BOL-52 | >300 | >300 | >300 | >300 | (300) |
| BOL-53 | 300 | >300 | >300 | 200 | >300 |
| BOL-54 | 300 | 300 | 300 | 200 | (200) |
| BOL-55 | 18.75 | 150 | 150 b | 12.5 | 4.7 |
| BOL-56 | >300 | >300 | >300 | >300 | >300 |
| BOL-57 | >300 | >300 | >300 | >300 | >300 |
| BOL-58 | >300 | >300 | >300 | >300 | >300 |
| BOL-59 | 75 | 200 | 200 | 100 | 150 |
| BOL-60 | 100 | 75 | 75 | 75 | 50 |
| BOL-61 | 18.75 | 25 | 37.5 | 75 | 6.25 |
| BOL-67 | 37.5 | 150 | 150 | 75 | 9.375 |
| BOL-68 | >300 | >300 | >300 | >300 | >300 |
| BOL-69 | 300 | >300 | >300 | 150 | >300 |
| BOL-70 | 150 | 200 | 300 | 100 | 100 |
| BOL-71 | >300 | (300) | >300 | >300 | >300 |
| BOL-72 | 75 | 50 | 50 | 75 | 75 |
| BOL-73 | 37.5 | 37.5 | 75 b | 50 | 150 |
| BOL-74 | >300 | 300 | >300 | >300 | 75 |
| BOL-75 | 300 | 300 b | 300 | 200 | 300 |
| BOL-79 | 4.7 | >300 | >300 | 4.7 | <=1.56 |
| BOL-80 | >300 | >300 | >300 | >300 | >300 |
| BOL-81 | (300) | 200 | (75) | >300 | 50 |
| BOL-82 | 18.75 | 75 | 75 | 9.375 | 6.25 |
| BOL-83 | >300 | >300 | >300 | >300 | >300 |
| BOL-84 | >300 | >300 | >300 | >300 | 300 |
| BOL-85 | >300 | >300 | >300 | >300 | >300 |
| BOL-86 | (300) | >300 | (300) | >300 | 200 |
| BOL-87 | 37.5 | 37.5 | 37.5 | 25 | 37.5 |

Values in parentheses designate a 75% inhibition of the growth of the microorganisms at the peptide concentration stated. A complete growth inhibition could not be achieved in this case.

Examination of the Cytotoxic Activity of Bolisin Analogues

Bolisin analogues having a good antimicrobial activity against at least one of the seven strains of microorganisms tested (MIC≦37.5 µg/ml) were selected for checking their cytotoxic activity.

In many cases, the ability of antimicrobial peptides to deposit on plasma membranes and permeabilize them is considered the mechanism of action of these substances. It is desirable that bacterial membranes are selectively damaged, hemoglobin were transferred to a 96 well microtitration plate with flat bottoms, and its absorption was determined at a wavelength of λ=450 nm in a microtitration plate reader. Incubation with a 1% solution of the surfactant Tween-20 served as a reference value for 100% hemolysis. Erythrocytes incubated only with test medium served as the negative control.

The hemolytic activity of bolisin analogues was stated on the basis of the total hemolysis by Tween-20 and calculated by the following formula:

$$\text{Hemolysis [\%]} = [A_{450\,nm}\,(\text{peptide}) - A_{450\,nm}\,(\text{negative control})] / [A_{450\,nm}\,(1\%\,\text{Tween 20}) - A_{450\,nm}\,(\text{negative control})] * 100$$

TSB medium with 287 mM glucose served as the test medium. The isotonic glucose concentration is to prevent non-specific hemolysis in a hypotensive medium (osmoprotection).

It is desirable that the peptides according to the invention exhibit no or but moderate lytic properties against erythrocytes. "Moderate lytic properties" means a lysis of less than 30% of the erythrocytes for the application of antimicrobially effective peptide concentrations.

Figure 1:
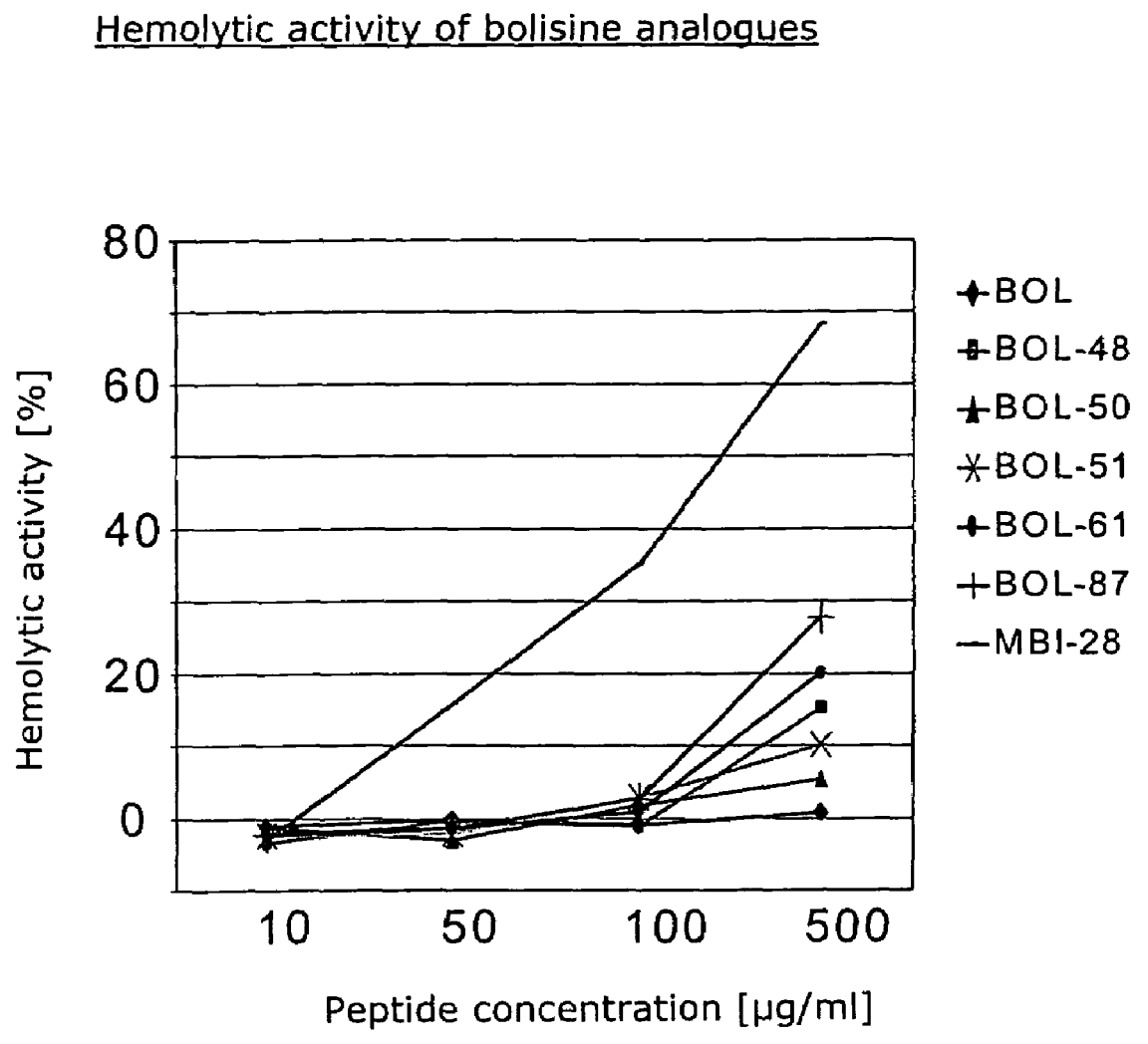

FIG. 1 shows that bolisin analogues in antimicrobially effective concentrations do not cause any hemolysis worth mentioning (<5%). Even at high concentrations (500 µg/ml), only a moderate lytic activity can be established (<30%). For comparison, the hemolytic activity of the antimicrobial peptide MBI-28 (Gough et al., 1996, Infect. Immun. 64(12): 4922-7) was plotted.

The invention claimed is:

1. An isolated peptide comprising the amino acid sequence of SEQ ID NO: 43.

2. The peptide of claim 1 wherein the peptide is conjugated to polymer.

3. The peptide of claim 1 wherein the peptide is conjugated to polysorbate.

4. A medicament comprising an antibiotically effective amount of the peptide of claim 1 in combination with a pharmacologically acceptable carrier or diluent.

5. A medicament comprising an antibiotically effective amount of the peptide of claim 2 in combination with a pharmacologically acceptable carrier or diluent.

6. A medicament comprising an antibiotically effective amount of the peptide of claim 3 in combination with a pharmacologically acceptable carrier or diluent.

7. The medicament according to claim 4 further comprising at least one ingredient, wherein the at least one ingredient is (i) an additional antibiotically effective ingredient (ii) an antivirally effective ingredient, an antiparasitically effective ingredient, or an antifungally effective ingredient.

8. The medicament according to claim 4 in an application form selected from the group consisting of an infusion, ointment, tablet, spray, and slow release capsule.

9. The medicament according to claim 5 in an application form selected from the group consisting of an infusion, ointment, tablet, spray, and slow release capsule.

10. A method for inhibiting the growth of a microorganism comprising contacting the microorganism with an antimicrobially effective amount of the peptide of claim 1.

11. A method for inhibiting the growth of a microorganism comprising contacting the microorganism with an antimicrobially effective amount of the peptide of claim 2.

12. A method for inhibiting the growth of a microorganism comprising contacting the microorganism with an antimicrobially effective amount of the peptide of claim 3.

13. A process for preparing the peptide according to claim 1 comprising expressing the protein in a prokaryotic or eukaryotic organism or chemically synthesizing the protein.

14. A method of using the peptide of claim 1 comprising administering an antimicrobially effective amount of the peptide to a patient in need thereof.

* * * * *

SEQUENCE LISTING

```
<160> NUMBER OF SEQ ID NOS: 56

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 1

Tyr Ile Val Tyr Lys Ile Arg Ser Ala Arg Lys Arg Ser Lys Ala Leu
 1               5                  10                  15

Lys

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 2

Tyr Ile Val Tyr Lys Ile Arg Ser Ala Asp Lys Arg Arg Lys Ala Leu
 1               5                  10                  15

Lys

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 3

Tyr Ile Val Tyr Lys Arg Arg Ser Ala Arg Lys Arg Ser Lys Ala Leu
 1               5                  10                  15

Lys

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 4

Tyr Ile Val Tyr Lys Arg Arg Ser Ala Asp Lys Arg Arg Lys Ala Leu
 1               5                  10                  15

Lys
```

```
<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 5

Tyr Ile Val Tyr Lys Ile Arg Ser Ala Arg Lys Arg Arg Lys Ala Leu
 1               5                  10                  15

Lys

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 6

Tyr Ile Arg Tyr Lys Ile Arg Ser Ala Arg Lys Arg Arg Lys Ala Leu
 1               5                  10                  15

Lys

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 7

Tyr

Lys

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 10

Tyr Ile Arg Tyr Lys Arg Arg Ser Ala Arg Lys Arg Arg Lys Ala Leu
 1               5                  10                  15

Lys

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 11

Tyr Ile Val Tyr Lys Ile Arg Ser Ala Pro Lys Arg Ser Lys Ala Leu
 1               5                  10                  15

Lys

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 12

Tyr Ile Val Trp Lys Ile Arg Ser Ala Asp Lys Arg Ser Lys Ala Leu
 1               5                  10                  15

Lys

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 13

Tyr Ile Val Tyr Lys Ile Arg Trp Ala Asp Lys Arg Ser Lys Ala Leu
 1               5                  10                  15

Lys

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 14

Tyr Ile Val Tyr Lys Ile Arg Ser Ala Trp Lys Arg Ser Lys Ala Leu
 1               5                  10                  15

Lys

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 15

Tyr Ile Val Tyr Lys Ile Arg Ser Ala Asp Lys Arg Trp Lys Ala Leu
 1               5                  10                  15

Lys

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 16

Tyr Ile Val Tyr Lys Ile Arg Ser Ala Trp Lys Arg Arg Lys Ala Leu
 1               5                  10                  15

Lys

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 17

Tyr Ile Val Tyr Lys Ile Arg Ser Ala Trp Lys Arg Trp Lys Ala Leu
 1               5                  10                  15

Lys

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 18

Tyr Ile Val Tyr Lys Ile Arg Ser Ala Arg Lys Arg Trp Lys Ala Leu
 1               5                  10                  15

Lys

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 19

Tyr Ile Val Tyr Lys Ile Arg Trp Ala Trp Lys Arg Ser Lys Ala Leu

```
                  1               5              10              15
Lys

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 20

Tyr Ile Val Tyr Lys Ile Arg Trp Ala Trp Lys Arg Arg Lys Ala Leu
  1               5              10              15
Lys

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 21

Tyr Ile Val Tyr Lys Ile Arg Trp Ala Arg Lys Arg Ser Lys Ala Leu
  1               5              10              15
Lys

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 22

Tyr Ile Val Tyr Lys Ile Arg Trp Ala Arg Lys Arg Arg Lys Ala Leu
  1               5              10              15
Lys

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 23

Tyr Ile Val Tyr Lys Ile Arg Trp Ala Arg Lys Arg Trp Lys Ala Leu
  1               5              10              15
Lys

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 24
```

Tyr Ile Val Tyr Lys Ile Arg Arg Ala Arg Lys Arg Lys Ala Leu
1               5                   10                  15

Lys

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 25

Tyr Ile Val Tyr Lys Ile Arg Arg Ala Trp Lys Arg Ser Lys Ala Leu
1               5                   10                  15

Lys

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 26

Tyr Ile Val Tyr Lys Ile Arg Arg Ala Trp Lys Arg Arg Lys Ala Leu
1               5                   10                  15

Lys

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 27

Tyr Ile Val Tyr Lys Ile Arg Arg Ala Trp Lys Arg Trp Lys Ala Leu
1               5                   10                  15

Lys

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 28

Tyr Ile Val Tyr Lys Ile Arg Ser Ala Lys Lys Arg Lys Lys Ala Leu
1               5                   10                  15

Lys

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 29

-continued

```
Tyr Ile Val Tyr Lys Ile Arg Ser Ala Lys Lys Arg Trp Lys Ala Leu
  1               5                  10                  15

Lys

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 30

Tyr Ile Val Tyr Lys Ile Arg Ser Ala Trp Lys Arg Lys Lys Ala Leu
  1               5                  10                  15

Lys

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 31

Tyr Ile Val Tyr Lys Ile Arg Trp Ala Lys Lys Arg Lys Lys Ala Leu
  1               5                  10                  15

Lys

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 32

Tyr Ile Val Tyr Lys Ile Arg Trp Ala Lys Lys Arg Trp Lys Ala Leu
  1               5                  10                  15

Lys

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 33

Tyr Ile Val Tyr Lys Ile Arg Trp Ala Trp Lys Arg Lys Lys Ala Leu
  1               5                  10                  15

Lys

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence:artificial
      bolisin analogue
```

```
<400> SEQUENCE: 34

Tyr Ile Val Tyr Lys Ile Arg Ser Ala Trp Lys Arg Trp Lys Ala Leu
 1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 35

Tyr Ile Val Tyr Lys Ile Arg Ser Ala Arg Lys Arg Trp Lys Ala Leu
 1               5                   10                  15

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 36

Tyr Ile Val Tyr Lys Ile Arg Ser Ala Trp Lys Arg Arg Lys
 1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 37

Tyr Ile Val Tyr Lys Ile Arg Ser Ala Trp Lys Arg Trp Lys
 1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 38

Tyr Ile Val Tyr Lys Ile Arg Ser Ala Arg Lys Arg Trp Lys
 1               5                   10

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 39

Tyr Ile Val Tyr Lys Ile Arg Trp Ala Arg Lys Arg Arg Lys Ala Leu
 1               5                   10                  15

<210> SEQ ID NO 40
<211> LENGTH: 14
<212> TYPE: PRT
```

```
<213> ORGANISM: Artificial Sequence
<220> FEATURE:
<223> OTHER INFORMATION: Description of Artificial Sequence:artificial
      bolisin analogue

<400> SEQUENCE: 40

Tyr Ile Val Tyr Lys Ile Arg Trp Ala Arg Lys Arg Arg Lys
  1               5                  10

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 41

Tyr Ile Val Trp Lys Ile Arg Ser Ala Arg Lys Arg Arg Lys Ala Leu
  1               5                  10                  15

Lys

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 42

Tyr Ile Val Trp Lys Ile Arg Ser Ala Trp Lys Arg Ser Lys Ala Leu
  1               5                  10                  15

Lys

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 43

Tyr Ile Val Arg Lys Ile Arg Ser Ala Trp Lys Arg Trp Lys Ala Leu
  1               5                  10                  15

Lys

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 44

Tyr Ile Val Arg Lys Ile Arg Ser Ala Trp Lys Arg Arg Lys Ala Leu
  1               5                  10                  15

Lys

<210> SEQ ID NO 45
<211> LENGTH: 17
<212> TYPE: PRT
<213> ORGANISM: Artificial Sequence
```

```
<220> FEATURE:
<223> OTHER INFORMATION: Description of Artificial Sequence:artificial
      bolisin analogue

<400

```
<213> ORGANISM: Artificial Sequence
<220> FEATURE:
<223> OTHER INFORMATION: Description of Artificial Sequence:artificial
      bolisin analogue

<400> SEQUENCE: 50

Lys Tyr Ile Val Tyr Lys Ile Arg Ser Ala Trp Lys Arg Arg Lys Ala
 1               5                  10                  15
Leu Lys

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 51

Lys Tyr Ile Val Tyr Lys Ile Arg Trp Ala Arg Lys Arg Arg Lys Ala
 1               5                  10                  15
Leu Lys

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 52

Tyr Ile Val Tyr Lys Ile Arg Phe Ala Phe Lys Arg Ser Lys Ala Leu
 1               5                  10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 53

Tyr Ile Val Tyr Lys Ile Arg Phe Ala Phe Lys Arg Arg Lys Ala Leu
 1               5                  10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 54

Tyr Ile Val Tyr Lys Ile Arg Trp Ala Trp Lys Arg Ser Lys Ala Leu
 1               5                  10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence:artificial
      bolisin analogue
```

-continued

```
<400> SEQUENCE: 55

Tyr Ile Val Tyr Lys Ile Arg Trp Thr Trp Lys Arg Ser Lys Ala Leu
  1               5                  10                  15

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence:artificial
      bolisin analogue

<400> SEQUENCE: 56

Lys Leu Ala Lys Arg Arg Lys Trp Ala Trp Arg Ile Lys Tyr Val Ile
  1               5                  10                  15
    Tyr
```